United States Patent
Sagüés et al.

(10) Patent No.: US 10,247,691 B1
(45) Date of Patent: Apr. 2, 2019

(54) SYSTEMS AND METHODS FOR CONTACTLESS ASSESSMENT OF REINFORCED CONCRETE

(71) Applicants: Alberto Antonio Sagüés, Lutz, FL (US); Michael Thomas Walsh, Tampa, FL (US)

(72) Inventors: Alberto Antonio Sagüés, Lutz, FL (US); Michael Thomas Walsh, Tampa, FL (US)

(73) Assignee: University of South Florida, Tampa, FL (US)

( * ) Notice: Subject to any disclaimer, the term of this patent is extended or adjusted under 35 U.S.C. 154(b) by 1550 days.

(21) Appl. No.: 13/905,761

(22) Filed: May 30, 2013

Related U.S. Application Data (60) Provisional application No. 61/653,012, filed on May 30, 2012, provisional application No. 61/771,991, filed on Mar. 4, 2013.

(51) Int. Cl.
*G01N 33/38* (2006.01)
*G01N 27/26* (2006.01)

(52) U.S. Cl.
CPC .................. *G01N 27/26* (2013.01)

(58) Field of Classification Search
CPC .................. G01N 17/02; G01N 17/04; G01N 17/006–17/046; G01N 27/26
See application file for complete search history.

(56) References Cited

U.S. PATENT DOCUMENTS

| | | | | |
|---|---|---|---|---|
| 3,626,341 A | * | 12/1971 | Dao | H01F 6/06 335/216 |
| 4,649,336 A | * | 3/1987 | Bindner | G01R 29/24 324/109 |
| 4,806,850 A | | 2/1989 | Saumade et al. | |
| 4,861,453 A | * | 8/1989 | Matsuoka | G01N 17/02 204/404 |
| 4,942,354 A | * | 7/1990 | Miller | G01N 17/02 204/404 |
| 5,136,247 A | | 8/1992 | Hansen | |
| 5,498,974 A | | 3/1996 | Verkuil | |
| 5,841,282 A | | 11/1998 | Christy et al. | |
| 5,945,594 A | * | 8/1999 | Kendig | G01N 3/32 204/404 |
| 6,856,159 B1 | | 2/2005 | Tolk | |
| 2002/0175892 A1 | | 11/2002 | Braun et al. | |
| 2003/0169058 A1 | | 9/2003 | Pierre et al. | |

(Continued)

OTHER PUBLICATIONS

Zhang et al., Corrosion Science, 2009, 2130-2138.*

(Continued)

*Primary Examiner* — Gurpreet Kaur
(74) *Attorney, Agent, or Firm* — Thomas | Horstemeyer, LLP (57) ABSTRACT

In one embodiment, non-contact assessment of reinforced concrete is performed by positioning a reference electrode in close proximity to a surface of the concrete without contacting the electrode to the surface, vibrating the electrode with a vibration generator, and measuring the electrical potential difference between the electrode and the concrete surface, the potential difference being indicative of the condition of a portion of a reinforcement member positioned below the concrete surface at the location of the electrode.

14 Claims, 8 Drawing Sheets

(56) References Cited

U.S. PATENT DOCUMENTS

| | | |
|---|---|---|
| 2003/0175945 A1 | 9/2003 | Thompson et al. |
| 2006/0122478 A1 | 6/2006 | Sliepen |
| 2010/0039127 A1 | 2/2010 | Orazem |
| 2013/0300419 A1 | 11/2013 | Hibbs |
| 2015/0185133 A1 | 7/2015 | Murray |

OTHER PUBLICATIONS

Yee et al., J. Electrochem. Soc. 1991, 55-61.*
Jamil et al., Electrochimica Acta, 2004, 2753-2760.*
Akid et al., J. Electrochimica Acta, 49, 2004, 2871-2879.*
Liu et al., Microelectronic Journal, 2008, 39, 802-806.*
Hu et al., Progress in Organic Coatings 2012, 73, 129-141.*
Huang, et al., "Monitoring Soil Contaminations Using a Contactless Conductivity Probe", Geophysical Prospecting, 1995, 43, 759-778.
Noras, "Non-Contact Surface Charge/Voltage Measurements" Capacitive probe-principle of operation. No. 3001, 2002, Trek, Inc.
Electric-Field Contact-Less Sensing System, Reference manual, MC33794.
Sagüés et al., "Contactless Kelvin Probe Electrode for Potential and Polarization Resistance Measurements of Reinforcing Steel in Concrete", Paper No. 4362, Corrosion 2014, NACE International, Houston, 2014, 1-9.
Walsh et al., "Novel Kelvin Probe electrode for non-intrusive corrosion rate evaluation of steel in aged concrete structures", in Proceedings of the 1st International Conference on Ageing of Materials & Structures, K. van Breugel and E.A.B. Koenders, Eds., Delft University of Technology, Delft, The Netherlands, 2014, 569-575.
Leonidas P. Emmenegger, "Contactless Electrode for Fast Survey of Concrete Reinforcement Corrosion" Transportation Research Board 94th annual meeting, Jan. 11-15, 2015, Washington, DC.—Session: 296, 1 page.
Sagüés et al., "Kelvin Probe electrode for contactless potential measurement on concrete—Properties and corrosion profiling application", Corrosion Science (2012) vol. 56, 26-35.
Student Poster "Application of a Macroscopic Kelvin Probe for Potential Survey of Reinforcement in Soil and Cementitious Filler" presented by W. Ruth during the NACE International Annual Meeting, Corrosion 2015, Dallas, Texas, Mar. 15-18, 1 page.
Student Poster "Application of a Macroscopic Kelvin Probe for Potential Survey of Reinforcement in Soil and Cementitious Filler" presented by W. Ruth at the American Institute of Chemical Engineers Southern Student Regional Conference, Clearwater Beach, FL, Apr. 10-12, 2015, 1 page.
Non-final Office Action dated Aug. 10, 2018 in U.S. Appl. No. 15/460,156.

* cited by examiner

SYSTEMS AND METHODS FOR CONTACTLESS ASSESSMENT OF REINFORCED CONCRETE

CROSS-REFERENCE TO RELATED APPLICATION(S)

This application claims priority to U.S. Provisional Application Ser. No. 61/653,012, filed May 30, 2012 and 61/771,991, filed Mar. 4, 2013, which are hereby incorporated by reference herein in their entirety.

BACKGROUND

The electrical potential distribution on the external surface of concrete can be indicative of various ongoing processes of interest. For example, surface potential mapping is often conducted to identify the location of corroding reinforcing steel. For that application, potential measurements are normally conducted by connecting the positive terminal of a high-impedance direct current voltmeter to the reinforcing steel assembly embedded in the concrete and the negative terminal to a reference electrode, typically a copper-copper sulfate electrode (CSE). The tip of the reference electrode is then placed in successive contact with an array of points on the external concrete surface and the potential for each point is recorded. The resulting potential map provides a diagnostic of the presence and position of regions of the reinforcement assembly with high likelihood of active corrosion.

The above-described method relies on the sizable potential transition (e.g., from about −150 millivolts (mV) to about −400 mV CSE) that formerly passive steel often experiences upon the onset of active corrosion. Thus, regions displaying negative potentials on the order of several hundred millivolts versus CSE may be considered suspect of active corrosion. If active corrosion affects only a portion of the steel, the potential is not uniformly highly negative on the concrete surface because of the finite resistivity of concrete that joins the active and the passive portions of the assembly. The steel in the latter portion is only partially polarized and potential measurements against nearby concrete remain only mildly negative, so the external potential map can reveal the location of the corroding zones as well. Because of measurement artifacts, the measured potentials may be more or less globally offset from those in an ideal case. Thus, identification of corroding regions often relies more on consideration of potential gradients rather than of the absolute potential values.

Concrete surface potential measurements are also conducted to perform corrosion rate measurements. Those measurements are polarization measurements in which the amount of impressed current needed to achieve a small potential change is determined. The current is impressed by means of an additional external electrode attached to the concrete surface or by means of rebar not in metallic contact with that being tested. Within certain limitations, the ratio of potential change to impressed current density yields the polarization resistance Rp, which is related to the corrosion current density $i_{corr}$ through the Stearn-Geary parameter B by the equation $i_{corr}=B/Rp$. The resulting value of $i_{corr}$ can then be related to the corrosion rate of the steel by the usual Faradaic conversion.

Surface potential measurements are sensitive to the condition of both the bulk of the concrete and its surface. For example, the presence of a carbonated concrete skin, even if it is very thin, can result in an appreciable potential difference (e.g., as much as 200 mV) between the outer surface and the bulk of the concrete. That difference reflects the widely different pH of pore water in the outer and inner regions. A diffusion potential (a general term that includes junction and membrane potentials as well as those resulting from other electrokinetic effects) develops to preserve charge neutrality upon coupled diffusion, across the region joining both zones, of anions (OH$^-$) and cations (K$^+$, Na$^+$) that have significantly different diffusivities. Weathering, sulfate attack, and other environmental interactions may cause similar electrochemical potential gradients that may affect the surface potential pattern. A very dry concrete surface may prevent accurate potential determination as the effective contact resistance begins to approach the value of the voltmeter input impedance. The sensitivity of the potential measurements to these phenomena creates both an opportunity for their characterization and a concern as a source of artifacts in the corrosion condition determination.

The extent to which potential measurement artifacts are present is obscured by the disruptive nature of the electrochemical reference electrode, which requires a shared electrolyte link between the metallic terminal and the concrete pore water. When the electrolyte tip of the reference electrode touches the concrete surface, a liquid transport process begins that transfers some of the electrode solution into the concrete pores and vice versa. The process may range from mostly interdiffusion if the concrete pores are nearly saturated, to strong convective capillary action if the pores are nearly dry. The latter case may result in appreciable drift in the voltmeter reading as the system slowly approaches a steady-state condition, likely involving the evolution of a diffusion potential pattern that includes both junction and membrane potential components. Such drift can introduce added uncertainty to the result of the potential measurement and significant artifacts in electrochemical corrosion rate measurements. A pre-wetting procedure is sometimes used for the concrete surface before placing the reference electrode to partially alleviate these effects, but comparable uncertainty exists as to the potential variation (and its time variation) created by the intrusion of the wetting fluid to the formerly dry concrete.

In addition to the above-described drawbacks of conventional potential measurement techniques, the process of conditioning (wetting) the concrete can be time consuming and labor intensive. In most cases, many (e.g., hundreds of) wet sponges must be applied to the concrete to be tested and often must be left in place for extended periods of time to achieve the level of saturation necessary to perform measurements.

In view of the foregoing discussion, it can be appreciated that it would be desirable to have an alternative system or method for assessing reinforced concrete.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an alternative system or method for assessing reinforced concrete. Disclosed herein are systems and methods that avoid one or more of the drawbacks of conventional reinforced concrete assessment systems and methods. In some embodiments, the disclosed systems utilize Kelvin probes to measure concrete surface electrical potentials so that a contactless measurement procedure can be performed that does not depend upon a shared electrolyte and that is inherently non-disruptive to the region sampled by the probe.

Furthermore, because the concrete need not be saturated with water to perform measurements, the disclosed systems enable faster and less labor-intensive measuring.

In the following disclosure, various specific embodiments are described. It is to be understood that those embodiments are example implementations of the disclosed inventions and that alternative embodiments are possible. All such embodiments are intended to fall within the scope of this disclosure.

Described herein is contactless, macroscopic Kelvin probe measurement of concrete surface potentials. The disclosure begins with a general discussion of the operation of a Kelvin probe and is followed by descriptions of example systems that incorporate Kelvin probes specifically designed to measure concrete surface potentials. Kelvin probes determine the potential difference E between two surfaces designated as the working surface and the reference surface, respectively. In the case of reinforced concrete, the working surface is a small part of the outer concrete surface and the reference surface is the surface on one side of a macroscopically small (e.g., approximately 1-centimeter (cm) diameter) electrode (e.g., disk) of a suitable metallic material, for example, gold or stainless steel with a stable passive film. The disk and the concrete surfaces are spaced a small distance h apart so as to approximate a parallel-plate capacitor configuration. The disk is electrically connected through electrical conductors (e.g., wires) to the reinforcement (e.g., steel bar assembly) embedded in the concrete. The steel bar surface is electrically connected to the external surface of the concrete by an electrolytic path provided mainly by the water in the concrete pore network. Consequently, the concrete and the reference surfaces are joined through an electronic and electrolytic conductive path with associated interfaces that determine the value of E. The relationship linking electrical charge Q and potential difference E across a capacitor with capacitance C is $$Q=EC \qquad \text{Equation 1}$$

For plates spaced by a small gap, the capacitance can be approximated by $$C=\varepsilon\varepsilon_0 A/h \qquad \text{Equation 2}$$

where $\varepsilon$ is the dielectric constant of the medium in the gap between the plates (normally air, $\varepsilon\sim 1$), $\varepsilon_0$ is the permittivity of vacuum, and A is the one-sided surface area of the smaller of the plates, in this case the reference surface. Because E is fixed by the characteristics of the intervening conducting and interfacial chain, if h is changed from one static position to another, the value of Q changes as well to satisfy Equations 1 and 2. In the Kelvin probe, h is varied cyclically with time by attaching the reference disk to the end of an electrically-insulating, longitudinally-vibrating stem. Consequently, Q changes cyclically as well, resulting in an alternating current $I_A$ circulating through the conductive path. If a potential source with a known potential E' selected at will is inserted in that path (e.g., into a break made in the connecting wire to the rebar), the potential between the reference and concrete surface becomes E+E'. When E'=−E, the potential across the capacitor is zero and the alternating current vanishes. This then permits determining the value of E by varying E' until $I_A=0$, a condition that can be reached with great sensitivity by adequate electronic amplification. The zeroing process can be made manually or performed automatically and promptly with ordinary control circuitry, yielding an immediate record of the value of E.

With interfaces having well-defined boundaries and locally-uniform electric charge profiles, the potential E measured by the Kelvin probe is the difference between the Volta (outer) potential $\Psi_R$ of the reference surface and the Volta potential of $\Psi_W$ of the working surface being examined $$E=\Psi_R-\Psi_W \qquad \text{Equation 3}$$

The metallic reference disk generally approximates those conditions and may be considered to have a well-defined, spatially averaged $\Psi_R$ value. The concrete facing is quite heterogeneous, as is the distribution in its pore network of the electrolyte responsible for much of the electric charge configuration in the material. Hence, $\Psi_W$ can be considered only as an effective value, that of an ideal conductor that would yield the same experimental results as those obtained with the concrete. Thus, $\Psi_W$ may be viewed as representing an approximate average of the potential of the surface of the concrete beneath the footprint of the reference surface disk. Lateral heterogeneity up to the millimeter scale (pore space-paste-fine aggregate domain) is expected to be reasonably averaged beneath the disk, but some sensitivity to the distribution of the coarse-aggregate, which is typically greater than 1 cm, can be anticipated.

Figure 1:
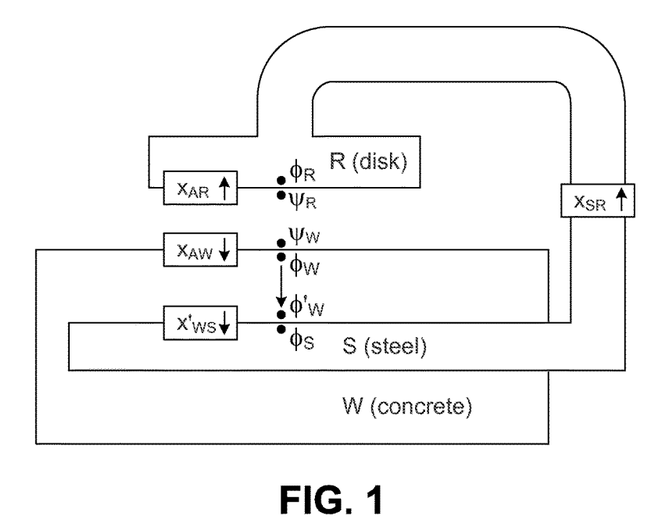
FIG. 1 is a schematic diagram that illustrates potentials and interfacial potential differences in a Kelvin probe arrangement for steel in concrete.

The value of E measured by the Kelvin probe can be determined by the system schematically illustrated in FIG. 1. For simplicity, only two different metals are assumed to be involved, one for the reference surface R and one for the steel bar S. The respective inner (Galvani) potentials are designated $\Phi_R$ and $\Phi_S$ with a corresponding interfacial potential difference $X_{SR}=\Phi_R-\Phi_S$. The arrows in the figure indicate that the stated difference of potential is added to the potential at the tail to obtain that at the head. Designations for the medium-air interfacial potential differences are respectively $X_{AR}=\Phi_R-\Psi_R$ and $X_{AW}=\Phi_W-\Psi_W$, and for the metal-electrolyte interfacial potential $X'_{WS}=\Phi_S-\Phi'_W$. Both $\Phi_W$ and $\Phi'_W$ are effective magnitudes representing a similar idealization as that noted above for $\Psi_W$. The values of $\Phi_W$ and $\Phi'_W$ are, in general, not the same because of the ohmic potential drop created by the corrosion macrocell currents in the concrete and of electrolyte composition gradients within the concrete that cause macroscopic junction potentials and electrokinetic effects. The resulting difference is designated as $\Delta\Phi_W=\Phi'_W-\Phi_W$. Ohmic drops and similar effects within the metals themselves are treated as negligible in the present analysis. Applying the above definitions to Equation 3 yields $$E=X'_{WS}+X_{SR}-X_{AR}+X_{AW}+\Delta\Phi_W \quad \text{Equation 4}$$

Figure 2:
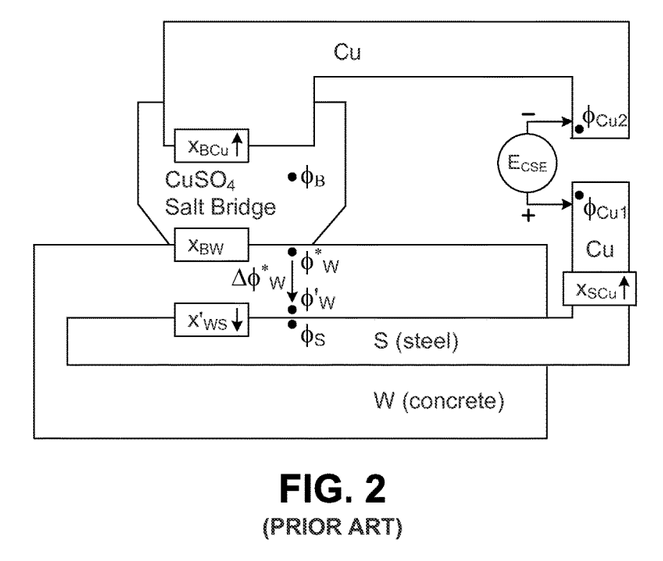
FIG. 2 is a schematic diagram that illustrates potentials and interfacial potential differences in a conventional reference electrode arrangement for steel in concrete.

A similar representation and nomenclature is presented in FIG. 2 for a conventional measurement of steel potential versus a regular reference electrode using a high impedance voltmeter. For simplicity, it is assumed that a Cu—CuSO$_4$ electrode (CSE) is being used and that all the connections involve Cu wiring, including the terminations of the voltmeter. In such a case, the Galvani and Volta potential differences between the voltmeter leads are the same and the measured potential $E_{CSE}$ is given by $$E_{CSE}=\Phi_{Cu1}-\Phi_{Cu2}=X'_{WS}+X_{SCu}-X_{BCu}+X_{BW}+\Delta\Phi^*_W \quad \text{Equation 5}$$

The salt bridge in FIG. 2 is assumed to include a porous plug as well as a wet sponge or similar accessory (not shown) positioned between the bulk of the CuSO$_4$ solution in the electrode and the surface of the concrete. The potential difference $X_{BW}$ incorporates any diffusion potentials or related phenomena associated with ionic concentration gradients across the plug and sponge. It is noted that the polarity chosen to designate $X_{BCu}$, a metal-to-electrolyte interfacial potential difference, was chosen for uniformity to match that used for $X'_{WS}$ so both variables adhere to the usual electrochemical convention.

Given its contactless character, placement of the Kelvin probe on the system should create no significant change of $X'_{WS}$ and $\Delta\Phi_W$ from their native values. Placement of the CSE and sponge should likewise be expected to have little effect on the value of $X'_{WS}$, at least when the concrete cover is not very thin and only moderate surface wetting is involved so the macrocell pattern is not substantially affected. However, the CSE placement is more disruptive of conditions near the external concrete surface. The concrete pore network in the contact region and to some distance beneath it is expected to be affected by intrusion of water and ions coming from the reference electrode and accessories, and from any pre-wetting applied to the surface of the concrete. As indicated above, the potential distribution in that region is altered to some extent relative to the initially dry condition, so $\Phi^*_W$ and $\Delta\Phi^*_W$ are used instead of the values without asterisk in the undisturbed case in FIG. 1.

The relationship between E and $E_{CSE}$ will be discussed next. From Equations 4 and 5 and treating $X'_{WS}$ as being invariant as indicated earlier, the potential measured by the Kelvin probe can be related to that measured in the usual manner with a CSE reference electrode by $$E=E_{CSE}+[(X_{SR}-X_{SCu})+(X_{AW}-X_{AR})+X_{BCu}+\Delta\Phi_W]+[-X_{BW}-\Delta\Phi^*_W] \quad \text{Equation 6}$$

The terms grouped within the first set of square brackets in Equation 6 are functions of the properties of metal-metal, metal-air, and metal-solution interfaces, and of the condition of the concrete in the undisturbed condition. Those quantities may then be considered on first approximation as being constants of the system and together contribute as a simple constant addition term to the conversion between E and $E_{CSE}$, at least for the particular place on the concrete surface being examined. In contrast, the terms within the second set of square brackets depend on the time evolution of the system as moisture and ionic species penetrate the region contacted by the wet-tip electrode and sponge, and are affected by pre-wetting. Thus, those terms are time-dependent and their effect on the total amount is to preclude relating E and $E_{CSE}$ through a simple time-invariant addition term. The variation should become very slow after a steady-state moisture and ionic species distribution is reached, but those processes may take a long time. In practical terms, for comparing Kelvin probe and conventional wet-tip electrode measurements, it is best to examine the system after a prearranged time after surface wetting started, when the time dependent terms have evolved to a roughly reproducible extent. That approach was adopted in the experiments described below.

The above analysis can be extended to compare the case of Kelvin probe measurements on a pre-wetted concrete surface with those performed conventionally on an equally pre-wetted surface. In that case both $X_{AW}$ and $\Delta\Phi_W$ become time-dependent as well, although $\Delta\Phi_W$ may be closer to $\Delta\Phi^*_W$ so the contribution of that pair could cancel to some extent. On the other hand, pre-wetting can also affect $X_{AR}$ due to adsorption of water on the reference disk due to evaporation from the freshly wet concrete surface. Thus, the timing of the Kelvin probe measurement at the moment of pre-wetting also needs to be noted for comparison between the Kelvin probe and conventional measurements when both involve a pre-wetted surface.

These considerations can be readily extended to any other reference electrode besides the CSE with appropriate substitution for $X_{SCu}$ and $X_{BCu}$ and for introduction of any pertinent additional metal-metal contact. The other terms and their significance remain the same as before.

Figure 3:
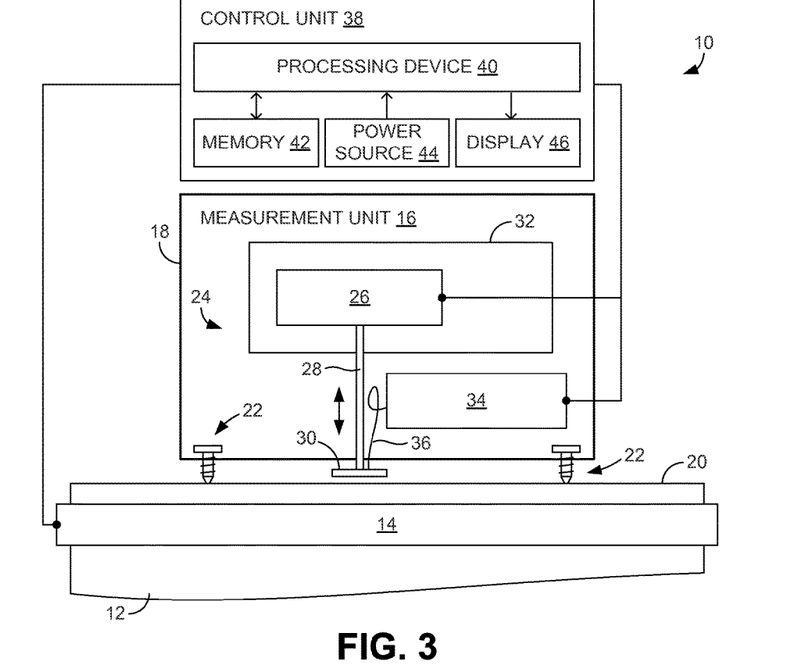
FIG. 3 is a schematic view of an embodiment of a non-contact reinforced concrete assessment system that includes a Kelvin probe.

FIG. 3 illustrates an example non-contact reinforced concrete assessment system 10 incorporating a Kelvin probe that can be used to identify possible corrosion of the steel reinforcement embedded within the concrete. In FIG. 3, the concrete 12 is part of a structure, such as a road or bridge, over which vehicle or human traffic can pass. The steel reinforcement is represented by a steel member 14 that is shown embedded within the concrete 12.

As shown in FIG. 3, the system 10 comprises a measurement unit 16 that includes an outer housing 18 made of a conductive material, such as steel. The measurement unit 16 is supported above an outer (top) surface 20 of the concrete 12 with adjustable feet 22 that can, in some embodiments, comprise one or more threaded screws. When provided, the adjustable feet 22 can be used to adjust the height of the measurement unit 16 relative to the concrete surface 20 as well as the gap between a reference electrode of the system 10 and the surface.

Supported by the outer housing 18 is a Kelvin probe 24 that comprises a vibration generator 26, a stem 28 that extends from the vibration generator, and a dry reference electrode 30 that is mounted to a distal tip of the stem. In some embodiments, the vibrating generator 26 comprises an electromagnetic voice coil that linearly displaces the stem 28, and therefore the reference electrode (see double-headed arrow), in response to a magnetic field generated from current passing through the coil. As is also shown in FIG. 3, the vibration generator 26 is electromagnetically shielded by a grounded inner shield 32, which can be made of steel or another electrically-conductive material.

The reference electrode 30 can comprise a small metal disk or alternatively shape element having a diameter or equivalent dimension ranging from several millimeters to several centimeters. Irrespective of its shape or size, the electrode 30 has a planar outer surface that faces the concrete surface. Example metals include pure corrosion-resistant metals, such as gold, and metal alloys, such as stainless steel, that require a passive film for corrosion resistance. The stem 28 can comprise a shaft of an insulating material that is not prone to static charge buildup, such as a polymeric material or wood. Provided within the housing 18 along with the vibration generator 26 is a preamplifier 34 that is electrically coupled to the reference electrode 30, for example with a conductive wire 36.

The reinforced concrete assessment system 10 further comprises a control unit 38 that controls operation of the system. While the control unit 38 can be separate from the measurement unit 16 as shown in FIG. 3, it is noted that, in some embodiments, the control unit and the measurement unit can be integrated into a single device. In the example of FIG. 3, the control unit 38 includes a processing device 40, memory 42, a power source 44, and a display 46. The control unit 38 is electrically coupled to the steel member 14, the vibration generator 26, and the preamplifier 34.

As shown in FIG. 3, the measurement unit 16 can be placed on top of the surface 20 of the concrete 12 that is to be evaluated. When the feet 22 of the unit 16 are properly adjusted, the reference electrode 30 will be approximately 0.9 to 1.1 mm from the concrete surface 20. When the system 10 is activated, for example by selecting an appropriate button on a user interface of the control unit 38 (not shown), the control unit enables current supplied by the power source 44 to flow to the vibration generator 26 so that it will linearly oscillate the reference electrode 30 toward and away from the concrete surface 20. In some embodiments, the reference electrode 30 moves within a range of approximately 0.8 to 1.2 mm between its uppermost and lowermost positions at a frequency of approximately 147 Hz.

As the reference electrode 30 oscillates, electrical signals from the electrode are amplified by the preamplifier 34 and captured by the control unit 38, which stores them within memory 42. Optionally, the signals are first processed by the processing device 40 to identify the electrical potential E represented by the signals. The electrical potential can also be displayed to the user with the display 46.

Experiments were conducted using a system similar to that illustrated in FIG. 3 to determine the feasibility, sensitivity, and stability of Kelvin probe measurements relative to conventional measurements. A Kelvin probe was constructed having a 13 mm diameter austenitic stainless steel (Type AISI 302) reference electrode disk that vibrated at 147 Hz with an approximately sinusoidal waveform of amplitude $h_A=0.5\pm\sim0.1$ mm (i.e., $1\pm\sim0.2$ mm peak-to-peak). This vibration was achieved using a voice coil electromagnetic driver. At rest, the reference-to-working surface distance was h=1 mm, so the closest nominal reference-to-working surface distance was $h_C=h-h_A=\sim0.5$ mm. The disk surface was ground to an 800 grit finish and periodically cleaned by gently brushing with a cotton-tipped applicator wetted with ethyl alcohol. The disk was placed at the end of a short stem made of wood to better dissipate static charging. A perforated metal casing was placed around the vibration generator and the preamplifier to provide shielding, leaving a 4 mm gap between the casing skirt and the concrete surface. Three insulated stop screws were positioned around the skirt perimeter and ensured stable positioning against flat surfaces. In addition, the screws permitted fine h adjustment when needed. The adjustment was to ±0.1 mm of the desired value by gaging against a flat machined surface. The experiments were performed against nominally flat and smooth concrete surfaces, which typically introduced less than 0.1 mm additional uncertainty in the value of h. However, the probe design could be optimized for more compact size and automatic working distance adjustment. The sensing circuit detected the off-zero current with a circuit that approached a zero-resistance-ammeter configuration. Zeroing was made automatically with a feedback circuit, and the value of E was acquired digitally. The probe output was electronically filtered with a low-pass filter with time constant $\tau\sim1$ s.

Figure 4:
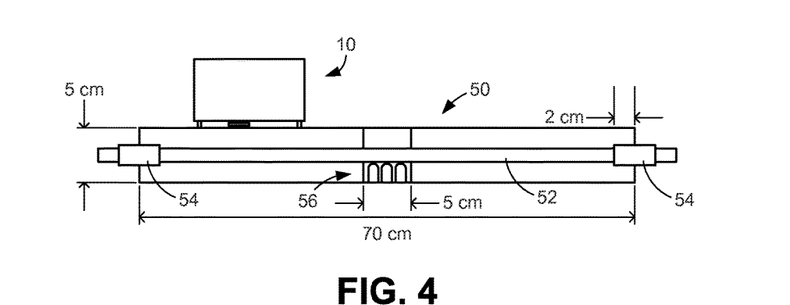
FIG. 4 is a schematic diagram of a reinforced concrete test specimen configuration and an example Kelvin probe placement.

As shown in FIG. 4, concrete prisms 50 that were 5-cm thick, 15-cm wide, and 70-cm long were made in using the mixture proportions listed in Table 1.

TABLE 1

| Constituent | Description | Amount |
| --- | --- | --- |
| Cement | Type I/II | 339 kg/m³ |
| Coarse Aggregate | Limestone ~2 cm max. | 1,017 kg/m³ |
| Fine Aggregate | ASTM C778 Graded Sand | 678 kg/m³ |
| Water (W/C = 0.5) | Tap Water | 169 kg/m³ |

The central 50 mm of the prism 50 contained 8.4 kg/m³ Cl⁻ ion admixed by adding the corresponding proportion of NaCl (13.9 kg/m³). Removable dams separated the Cl⁻-admixed region from the rest while casting the concrete. The dams were removed just before final consolidation resulting in a continuous joint. Wooden molds with a thin-mold release cover were used. The slabs were cast so that five surfaces were form-cast and the remaining one (a broad face) was free and hand finished.

Each specimen had a longitudinally centered #4 (13-mm diameter) plain steel ASTM A-615 reinforcing steel bar 52 with dark mill scale with the last 13 mm inside concrete on each end as well as any emerging steel covered with epoxy 54 to avoid exit line corrosion.

All Kelvin probe and conventional wet-tip electrode tests were performed on the broadest form-cast surface of the specimens. The form-cast surfaces were macroscopically flat, but finely rough as is typical of a wood form finish.

The specimens were covered to prevent evaporation and demolded approximately 4 days after casting. Curing inside plastic bags with excess water continued until 4 weeks after casting, after which the specimens were left exposed to laboratory air, approximately 60% relative humidity (RH) and approximately 24° C. Initial conventional surface potential surveys confirmed the presence of an actively corroding central region on the rebar, coinciding with the chloride-contaminated concrete. However, potential differentiation between the central anodic region and the rest of the surface was modest (e.g., less than 150 mV) and tended to lessen with increasing drying of the specimens. To increase differentiation after approximately 12 weeks of exposure to laboratory air, the specimens were re-moisturized in closed wet bags for approximately 2 weeks. The specimens were then modified on the hand-finished surface (on the opposite side where the potential measurements were made) by drilling in the chloride-contaminated zone with a masonry drill three equispaced 1-cm diameter holes 56, just reaching the rebar surface. Approximately 1 cm³ of NaCl-saturated water was placed in each hole and allowed to partially absorb in the surrounding concrete. The holes were filled with paper soaked with the same solution and covered with duct tape. Measurements conducted during the following 1-2 weeks on the opposite form-cast surface revealed greater than 200 mV potential differentiation in the potential profiles of the two duplicate specimens. The potential measurements described herein correspond to that period.

Potential profiles were obtained with the Kelvin probe on the dry and pre-wetted concrete surface conditions and with a conventional reference electrode on the pre-wetted concrete surface condition as well as on dry concrete for selected tests. The conventional electrode was a saturated calomel electrode (SCE). This electrode was chosen instead of the CSE commonly used for concrete tests to rule out any possible artifacts from the $CuSO_4$ stains often left by the latter. The SCE uses a fine glass frit electrolyte channel that allows only vestigial KCl contamination, while having low enough impedance to be unaffected by the FET-input front end of the data logger system used with that electrode. The tip of the SCE was surrounded by a 3-mm thick sponge sheet wetted with tap water of approximately 2000 ohm-cm resistivity. For the pre-wetted condition measurements, the surface of the concrete was dabbed on the test spots with a tap-water-soaked sponge. Any free surface water was blotted off. As indicated above, the overall provisions in comparing measurements from Kelvin probe and conventional measurements still apply if the SCE is used instead of the CSE.

Potential profile measurements were performed on the broad form-cast surface, on top of the rebar, at the center of the face, and at 2.5-cm intervals on either side for the SCE and 1.25-cm intervals for the Kelvin probe. The probe or electrode output was recorded with a data logger approximately 5 seconds after placement in the test spot.

For profile measurements on the dry surface condition, the specimen was allowed to dry in lab air overnight from any previous test involving wetting. For pre-wetted condition profile measurements, the SCE or Kelvin probe was placed and the potential was read on each spot typically within approximately 20 seconds after the spot was prewetted. Repeat potential profiles were conducted approximately 10 minutes after the first.

Figure 5:
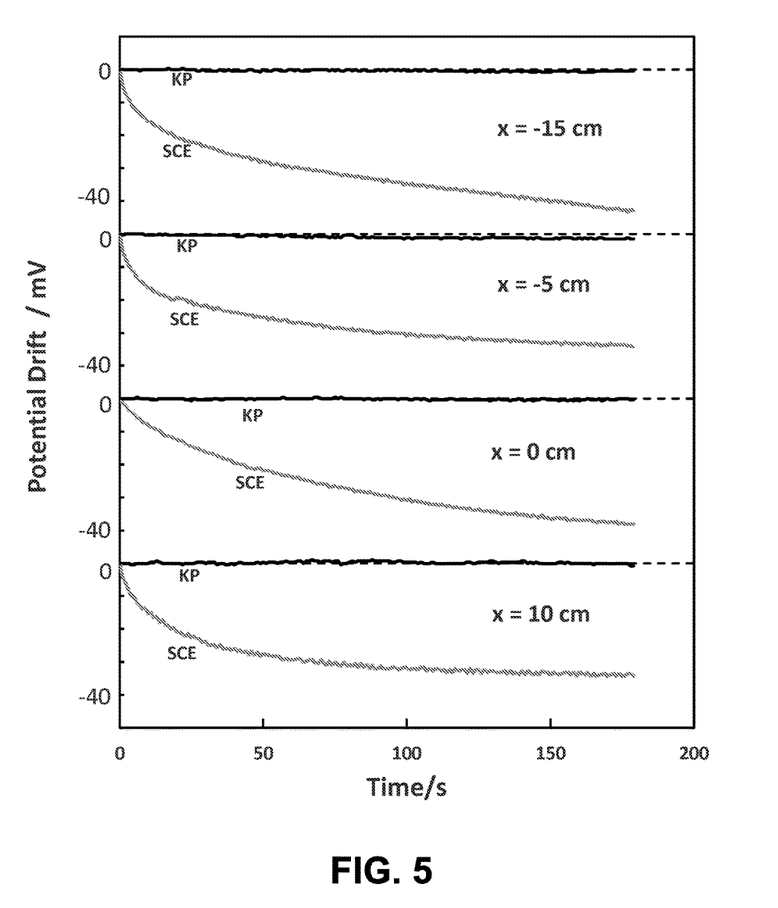
FIG. 5 comprises graphs that illustrate the stability of measured potential for a Kelvin probe and a conventional electrode (SCE), shown as drift from value measured 1 second after probe placement on dry concrete.

When placed on an undisturbed concrete surface in steady atmospheric contact, the Kelvin probe provided nearly instantaneous and far more stable readings than those possible with a conventional wet-tip reference electrode. FIG. 5 shows typical time records of the output of the Kelvin probe following placement on the surface of a reinforced concrete specimen that had been left in laboratory air for several days/weeks after curing. The tests were conducted at least one day after any previous temporary wetting of the surface for SCE measurements. The records correspond to transfer of the probe onto the concrete surface from rest on another point on the concrete surface that had a different potential. Primary stabilization to the new potential took approximately 1 second, reflecting the time constant of the electronic filtering circuit. The graphs show the potential drift as a change of output relative to the value obtained at a moment 1 second after probe placement in the new position. That moment was designated as time=0. The output for time greater than 0 remained constant typically within ±1 mV for an evaluation period of 3 minutes as long as the probe sensing disk assembly and underlying concrete surface remained undisturbed. Warm or moist air briefly blown on the sensing area caused potential excursions of up to several mV that vanished a few seconds after the disturbance ended.

FIG. 5 also shows for comparison the potential evolution observed when placing afterwards on the same point the SCE with its wet sponge tip, but without pre-wetting the surface. As it is commonly observed in such cases, there was considerable drift of the output, reflecting electrolytic rearrangement in the pore network of the concrete near the surface as it is invaded by the water from the sponge, with consequent slow establishment of a new diffusion potential regime. In the context of Equation 5, those changes reflect variations in $\Delta\Phi^*_W$ and $X_{BW}$. The causes and direction of those changes are addressed in the discussion on potential profiles below. The extent of drift (e.g., up to greater than 40 mV in 3 minutes) greatly exceeded that encountered with the Kelvin probe and in most instances the output had not visually stabilized during the recording interval.

For media with sufficient presence of mobile charge carriers, the position of the working surface from the standpoint of the operation of a macroscopic Kelvin probe is effectively the same as the geometric outer surface of the material. For a porous material like concrete, electric charge transport is dominated by the pore solution which normally is highly conductive and partially fills the pore network. The solid aggregate cement paste matrix has properties that approach those of a porous dielectric with vestigial conductance. For moist concrete, appreciable amounts of pore water are expected to exist right up to the concrete outer surface so it is clearly the working surface. For concrete long exposed to air of moderate relative humidity, the electrolyte presence in the pore network may be very small due to evaporation, and the conductivity of the remaining electrolyte may also be much diminished due to reaction with atmospheric $CO_2$. Depending on the concrete age and external humidity those effects reach depths ranging from only a few μm to as much as many cm. It was desired to determine to which extent the Kelvin probe working surface coincided with the geometric outer surface for concrete in various conditions.

Figure 6:
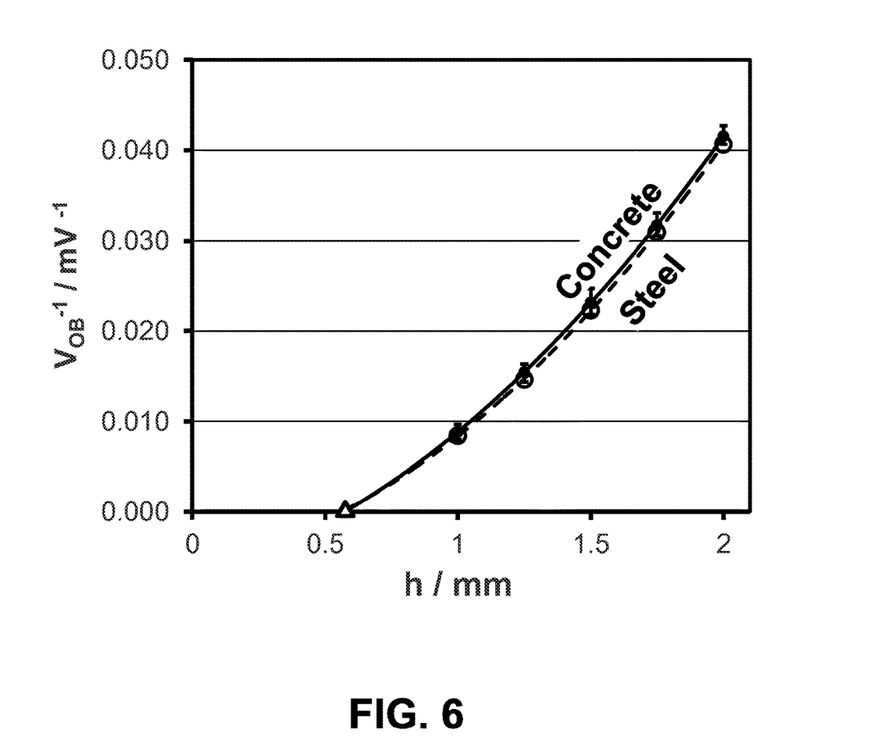
FIG. 6 is a graph that illustrates the determination of effective working surface position.

To examine that issue, measurements were conducted with the Kelvin probe zeroing circuit intentionally deviated, by 1 V, out of the balance condition. In that condition, the alternating current generated by the probe has its main spectral component with frequency equal to the vibrating frequency and amplitude approximately inversely proportional to $h_C$. The Kelvin probe circuit reports that current after amplification as an alternating current potential, of which the root mean square (RMS) value, $V_{OB}$, was measured and recorded. When the effective working surface coincides with the outer material surface, a plot of $V_{OB}^{-1}$ as function of h should yield a curve that on extrapolation intersects the h axis at $h=h_A$ since at that condition the reference surface would virtually contact the working surface with ideally unlimited output amplitude. If the effective working surface were deeper than the external surface, the curve for $V_{OB}^{-1}(h)$ would be expected to shift to the left compared with the previous case and have an extrapolated intersection to the left of $h_A$.

As a baseline, the value of $V_{OB}$ was measured when the Kelvin probe reference was placed on a flat-machined smooth steel surface at the normal h=1 mm working distance, and also after increasing h to 1.25, 1.5, 1.75 and 2 mm. The same procedure was conducted at various points on the surface of the concrete prisms when they had had been left in laboratory air for several days/weeks after curing. Similar tests were conducted with three other available reinforced concrete specimens that had been allowed to dry in laboratory air for over a decade after a previous investigation. The composition of the concrete in those specimens corresponds to mixes A, E, and F as detailed elsewhere.

FIG. 6 shows the resulting $V_{OB}^{-1}(h)$ graphs. The results for steel could be closely fit to a second-degree polynomial relationship with a modest quadratic component. The h-axis intercept of the fit function (average of two tests) was approximately 0.56 mm, closely approaching the value of $h_A$=0.5 mm expected for a metallic surface, considering the 0.1 mm uncertainty affecting both h and $h_A$. The curves for concrete, regardless of composition or age, all deviated very little from the shape and position of the curve obtained for steel. Because of the close superposition, only variation bands are shown, indicating the range of $V_{OB}^{-1}$ values obtained for the concrete specimens. The greatest corresponding leftward horizontal deviation from the steel curve was only approximately 0.1 mm, which is well within the overall variability in h especially since in concrete specimens, some surface deviation from a fully flat surface is common. The h-axis intercept of the fit for the concrete specimens was virtually the same as that for the steel surface. It was thus concluded that the concrete geometric outer surface coincided with the Kelvin probe working surface, at least within the operating positioning precision. That result applied even for concrete that had aged extensively under the type of moderately dry atmospheric conditions that lead to high surface resistivity values (e.g., greater than 1 MΩ-cm).

Spurious surface and spatial electric charges exist in the supporting structure and other conductors near the vibrating disk inside the shielding enclosure. Those charges modify the electric field created by the working surface so that the nulling potential differs from that which would have been obtained in the absence of the spurious sources. The effect is relatively stronger the farther away the disk is from the working surface, so the result of the Kelvin probe measurement becomes sensitive to the average probe-to-working surface distance. The extent to which this artifact existed in the present system was determined by varying the distance between the probe supports and the concrete surface by means of spacers and measuring the resulting change in output.

The effect was found to be small, in the form of a shift in measured potential in the positive direction typically ranging from nil to less than 40 mV when increasing h from 1 mm to 2 mm, a change much larger than the usual variability of h. Within that 1 mm range, the precise magnitude of the shift varied depending on recent history of maintenance of the disk supporting assembly and cleaning of the internal surface of the shielding enclosure. For any given such condition, the shift was approximately linearly dependent on the increase in working distance and of the same order when measuring either a flat-machined smooth steel surface or concrete.

Potential measurements conducted at various points of the concrete surface over a single piece of reinforcement with various polarization conditions along its length will be discussed next. Before addressing those results, however, it is noted that other tests were conducted with the Kelvin probe placed at a fixed position on the dry surface of the specimens that had multiple, non-interconnected metallic electrodes (the same specimens from a previous investigation noted earlier). In those tests, the Kelvin probe yielded, as expected, potential values for the various electrodes that differed from each other by the same amount as that determined by direct measurement with a high impedance voltmeter. The agreement was within the ±1 mV resolution and overall percent accuracy of the digital displays of the voltmeter and the Kelvin probe, as long as the switching of the Kelvin probe connection from one electrode to the other was performed promptly so minor drift effects such as those shown in FIG. 5 did not introduce additional error.

Figure 7:
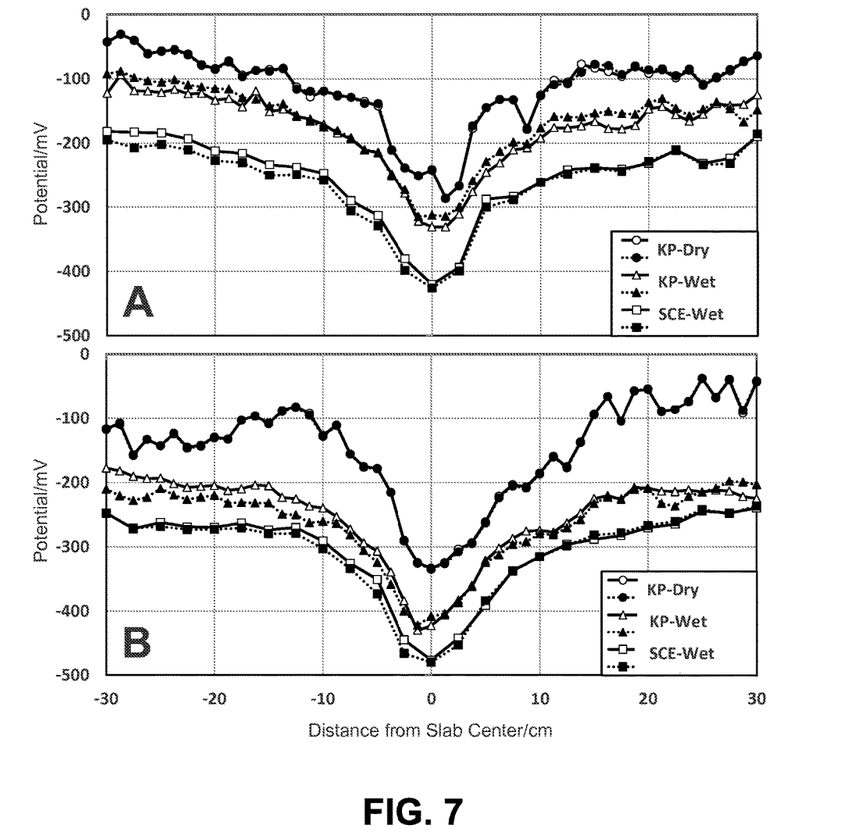
FIGS. 7A and 7B comprise graphs of potential profiles obtained in reinforced concrete slabs illustrating overall trends and variation between replicate slabs A and B.

FIG. 7 shows potential profiles obtained with the Kelvin probe and with the SCE for each of the duplicate longitudinal rebar specimens. The results correspond to the condition described above, shortly after modification on the backside of the specimens, to obtain a strongly evidenced central corroding region. In each specimen, the first set of measurements was taken in the dry surface conditions with the Kelvin probe proceeding from one end of the slab to the other and then repeated immediately. The surface of the slab was then topically moistened at the intended test spots and a second set of duplicate measurements was taken using the SCE with the wet sponge tip. Afterwards, the surface topical moistening was refreshed and a final set of duplicate measurements was taken on the moist spots with the Kelvin probe. The duplicate results for the three sets of measurements are labeled Kelvin probe-Dry, SCE Wet and Kelvin probe-Wet, respectively.

The results from both slabs were comparable within the variability levels commonly encountered with assessing corrosion phenomena in concrete. The following discussion addresses the short-term repeatability in immediately consecutive profile measurements within a given slab and the overall features of the potential profiles.

Regarding short-term repeatability, the Kelvin probe Dry data showed closely overlapping consecutive profiles along the entire length of the specimen, consistent with the nearly constant output noted in FIG. 5 for the Kelvin probe placed on a stabilized dry concrete surface. The SCE Wet data showed greater variability in consecutive results than those for Kelvin probe Dry data, reflecting spot-to-spot variations in time-dependent water absorption and evaporation following the pre-wetting. The changes, which can be interpreted as noted earlier in the context of Equation 5, were in the same order as those shown in the time charts in FIG. 5 for the SCE data after the first minute or so of placing the wet sponge on a previously dry concrete surface. When the Kelvin probe was placed on the pre-wetted locations, the consecutive measurements on the same spot showed variability greater than that for the Kelvin probe in the dry condition and comparable to that in the SCE Wet data. As in the SCE measurements, that variability is interpreted as being associated with moisture evolution with time at the pre-wetted spots on the concrete surface, affecting $X_{AW}$ and $\Delta\Phi_W$. As noted earlier, minute changes in the amount of water adsorbed on the reference disk surface, given its proximity to the freshly evaporating concrete surface, may have contributed to the variability as well through changes in $X_{AR}$.

Regarding the overall features, the SCE profiles showed the distinct negative dip pattern, in the present case approximately 200 mV deep, expected from a concrete slab with a centrally corroding segment on a longitudinal reinforcing bar. FIG. 7 shows that the Kelvin probe profile shape and range, for both the dry and wet conditions, generally reproduced the SCE pattern. This is manifested in the graphs in FIG. 8, which show linear correspondence with slopes ranging from 0.87 to 1.12 and correlation coefficients ranging from 0.87 to 0.96. The corresponding offsets from an ideal 1:1 coincidence with the CSE readings were about +100 to +200 mV for the Kelvin probe Dry condition and about half as much for the Kelvin probe Wet condition. Comparison of the profiles is conceptually more straightforward for the Wet cases, where both probes interacted with a concrete surface in the same nominal condition and measurement timing was similar. Assuming on first approximation a correlation slope of unity, the potential offset for the wet cases may be viewed as a temporary calibration of the Kelvin probe readings with respect to potential measurements in the SCE scale, corresponding ideally to the addition of the terms in square brackets in the equivalent of Equation 6 for an SCE.

The calibration should be viewed as temporary because even if the timing of the measurements with respect to the moment of wetting were strictly controlled, day-to-day variations in environmental variables as well as long term evolution of the concrete surface are expected to appreciably affect the key parameters in Equation 6. In particular, the value of $X_{AR}$ (as treated in the simplified treatment used here) is highly sensitive to the makeup of a region only a few atomic distances thick on the disk surface. Even if the disk had been recently cleaned, monolayer-levels of moisture or organic vapor precipitation on the surface can readily build up with time of exposure to normal environmental conditions, leading to potential changes that can be large (e.g., greater than 100 mV). Variations of that order were noted during testing conducted at different times, especially if servicing of the probe disk was involved. Consequently, if absolute as well as relative potential profile information were sought with the Kelvin probe, a fresh calibration step should be conducted concurrent with the measurements.

Figure 8:
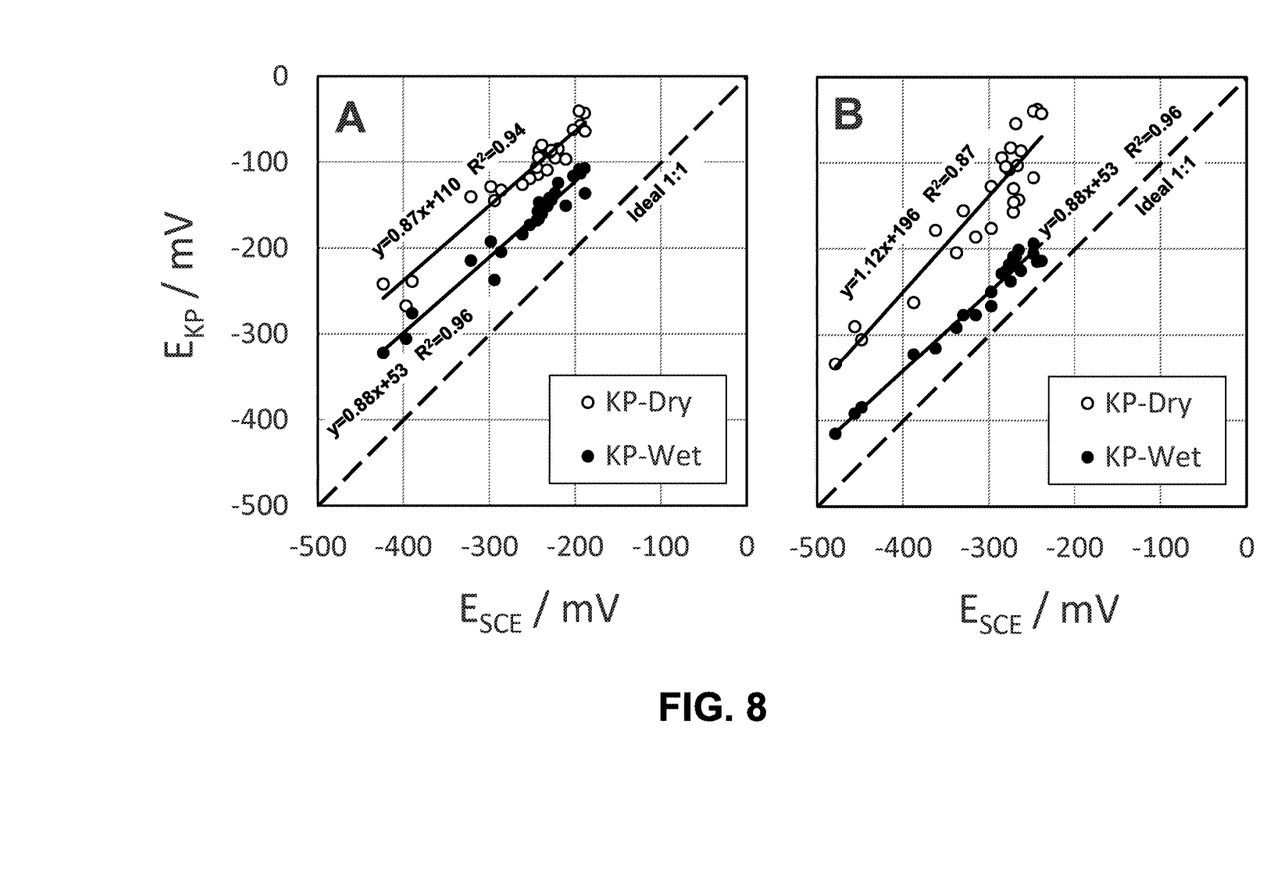
FIGS. 8A and 8B comprise graphs of the correlation between potentials measured with an SCE (on a pre-wetted concrete surface) and a Kelvin probe on the concrete surface in the dry and wet conditions, illustrating overall trends and variation between replicate slabs A and B.

The Kelvin probe Dry surface profiles were, as exemplified in FIGS. 7 and 8, usually positively offset with respect to those obtained in the Wet condition. This shift is in the same direction as that documented for the SCE in FIG. 5 by comparing the potential obtained at very short times, when the concrete surface was only beginning to depart from its initial dry condition, to the more negative values prevalent after substantial water absorption from the sponge took place. Such change may be interpreted as due to the slow dissipation of a diffusion potential (manifested in the combined values of $X_{AW}$ and $\Delta\Phi_W$ or $X_{BW}$ and $\Delta\Phi^*_W$ in Equations 4 or 5, respectively) due in part to a gradient in $OH^-$ concentration in the water partially filling the pores. The $OH^-$ concentration of the pore water has high values inside the concrete, due to high alkaline content, and smaller values near the surface because of carbonation by interaction with atmospheric $CO_2$. In this interpretation, the higher diffusivity of the $OH^-$ ions compared with that of the balancing cations promotes a diffusion potential difference where the outer surface is more negative than the inside. Because of the polarity of the Kelvin probe and SCE measurements, the result is a more positive steel potential reading than if the diffusion potential were not present. Other electrolytes, such as those associated with chloride salts, would have additional individual effects. As water refills the partially empty pore network near the surface, the resulting enhanced transport between outer and inner regions lessens solute concentration gradients, hence reducing the magnitude of the junction potential difference and resulting in a shift in the negative direction of the measured potential.

The Kelvin probe Dry surface profiles also showed more spatial variability than those for the Wet condition. Because of the high reproducibility noted above, the spatial variability represented true local potential differences on dry regions 1.25 cm apart. The source of the short distance variability is yet to be identified in follow-up work. In that context, it is noted that the Kelvin probe Wet profiles tended to show less short-distance spatial variability than for the dry condition. It may then be proposed that the local variations in the dry case are associated with variations in diffusion potential from local changes in the degree of carbonation, or differences in the evaporative concentration at the extreme outer surface of other species with similar outcome. Some of the differences may be associated with how close to the surface the coarse aggregate may be locally. Those effects would diminish upon pre-wetting as discussed earlier, resulting in a smoother potential profile than that in the dry condition.

The experimentation described above demonstrates the practical feasibility of Kelvin probe measurement of potential on the concrete surface, with very low drift on dry concrete surfaces and sufficient sensitivity for detailed potential mapping. An especially attractive feature of the Kelvin probe is its ability to perform essentially instantaneous and non-intrusive measurements, requiring neither direct contact with the surface nor prior surface preparation in the form of wetting plus stabilization. The output sensitivity to disk-to-surface distance is modest, which is desirable for practical use on regularly finished concrete surfaces.

The Kelvin probe therefore merits consideration as an alternative to wet-tip contacting reference electrodes for conducting potential survey of bridge decks or similar structures without the need for laborious maintenance of wet contacts. Given its speed, stability, and absence of contact with the concrete surface, the Kelvin probe or an array thereof may be particularly suitable for adaptation to automatic operation trailed from a slow-moving vehicle for minimum traffic disruption. Measurement scatter introduced by the probe sensitivity to the surface condition of itself and of the concrete, especially in the presence of contaminant spills or other commonly occurring alterations of the structural surface, as well as the sensitivity to surface roughness, may be reduced in such an application by using a larger reference disk and a higher disk-to-surface distance. Such modifications provide for spatial averaging of the output with consequent filtering of short-distance variations and can be implemented by hardware scaling with readily available technology.

The Kelvin probe also holds promise as a highly stable reference electrode for measurements of polarization resistance or of low frequency electrochemical impedance of reinforcement, especially when the concrete surface is dry and it is desired not to disturb it. In those cases, wet-tip electrode potential drift, as well as the effect of any moisture applied to the concrete near the reinforcement for surface preparation, could lead to appreciable measurement artifacts. The use of the Kelvin probe together with a non-wetting counter electrode (such as a conductive elastomer) would obviate those concerns. Polarization tests of this type involve measuring only relative potential changes at a single point on the surface, so sensitivity to spatial variations in concrete surface condition is not an issue such as it was for potential mapping.

In its present form, the Kelvin probe requires, for either of the above applications, a ground contact to one point in the normally electrically continuous reinforcing steel assembly of the structure to be assessed. For traveling probes, that connection should be implemented beforehand, so the entire structure could be sampled using a temporary flexible extension cable. In potential mapping, the identification of corroding spots may be sufficiently established, if the surface potential gradients are large enough, solely by means of differential potential measurements that ideally do not need a ground contact. That approach can be implemented with wet-tip reference electrodes if they and the underlying concrete have sufficiently low impedance to keep electrical noise at acceptable levels.

While a source of scatter in the case of potential mapping applications, the high sensitivity of the Kelvin probe to the condition of the concrete surface offers a powerful alternative to investigate phenomena for which a wet-tip electrode would be too disruptive. Among other applications, the Kelvin probe with appropriate customization may be able, for example, to (i) measure the evolution of the early stages of concrete carbonation in real time by monitoring the associated diffusion potential development, a sensitivity that applies also to the following; (ii) detect moisture content gradients that would have been otherwise overwhelmed by contact with a wet electrode tip; (iii) detect diffusional penetration and partition of moisture and chemical species such as chloride ions between aggregate and hydrated cement paste in concrete cross sections; (iv) assess the transport and distribution of migrating corrosion inhibitors in concrete; (v) characterize the penetration and aging of concrete surface treatments such as silane/siloxane compounds; (vi) characterize the extent of evaporative concentration of species such as chloride ions on the external concrete surface; (vii) assess sulfate attack; (viii) assessment of concrete surface contamination and the effectiveness of cleaning and remediation methods.

Figure 9:
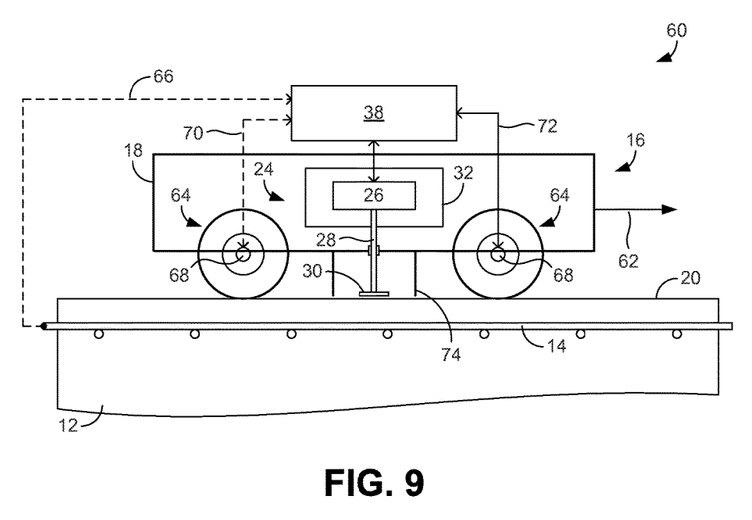
FIG. 9 is a schematic side view of a second embodiment of a non-contact reinforced concrete assessment system that includes a Kelvin probe.
Figure 10:
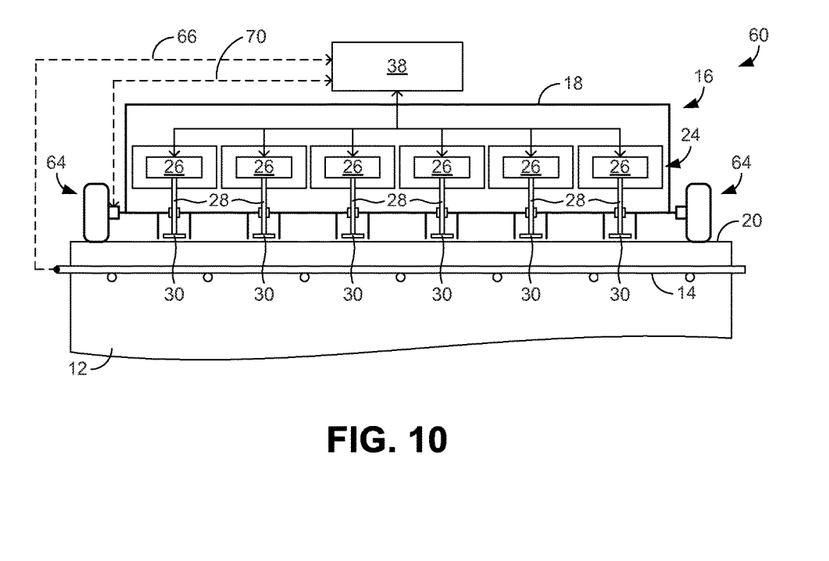
FIG. 10 is a schematic end view of the non-contact reinforced concrete assessment system of FIG. 9.

As described above, Kelvin probes can be applied to automatic operation trailed from a slow-moving vehicle for minimum traffic disruption. FIGS. 9 and 10 illustrate an example non-contact reinforced concrete assessment system 60 that can be used in such an application. As is apparent from these figures, the system 60 is similar in many ways to the system 10 shown in FIG. 3. Accordingly, with reference to FIG. 9, the system 60 also comprises a measurement unit 16 that includes an outer housing 18 and a Kelvin probe 24 that comprises a vibration generator 26, a stem 28, and a dry reference electrode 30. A preamplifier (not shown) can also be provided within the housing 18. In addition to the measurement unit 16, the system 60 includes a control unit 38 that, for example, can include a processing device, memory, a power source, and a display.

Unlike the system 10, however, the system 60 is adapted to be pulled by a slow-moving vehicle in the direction indicated by the arrow 62. Accordingly, wheels 64 are mounted to the measurement unit 16 to enable it to be pulled along the concrete surface 20 in similar manner to a conventional trailer. As is further illustrated in FIG. 9, the control unit 38 can be electrically coupled to the steel member 14 embedded in the concrete 12 with an electrical conductor 66 in similar manner to that shown in FIG. 3. In such a case, the system 60 operates in an absolute mode in which all measurements are taken relative to the same reference. Alternatively, in cases in which the wheels are electrically conductive (e.g., when the wheels have electrically-conductive elastomeric tires), the control unit 38 can be electrically coupled to the wheel's axle 68 with a different electrical conductor 70 so that measurements can be taken in a differential or relative mode. In such a mode, the measurements are taken relative to different reference points along the concrete surface 20 (i.e., the points on the surface with which the wheel 64 is in contact. In such a case, the nature of the contact with the concrete 12 does not matter as it is nulled out by the circuitry. The measurements taken at different points along the surface can then be compared to each other as a means of identifying hot spots that are indicative of active corrosion. Such a mode may be a more attractive alternative from the point of view of operation speed because this mode does not require a trailing wired contact to the rebar assembly and the rolling system is completely self-contained. The differential mode may also be of use for surveying decks constructed with epoxy-coated rebar (ECR), where the assembly is not reliably interconnected. While interpretation of potential maps for ECR is subject to considerable uncertainty, variation of potential patterns with time in successive assessments may provide an added tool for nondestructive detection of corrosion there.

Because measurements are taken at multiple points along the length of the concrete surface 20, it is important to determine where each measurement was taken. To this end, the control unit 38 can be electrically coupled with another electrical conductor 72 to a distance measurement device (not shown) mounted to the axle 68 of one of the wheels 64. With such a device, the angular position of the wheel 64 at the point at which each measurement is taken can be recorded and, with knowledge of the diameter of the wheel 64, can be converted into a linear distance.

As is further shown in FIG. 9, the measurement unit 16 can also include a grounded shield 74 that shields the electrode 30 from electromagnetic interference. In some embodiments, the shield 74 comprises a cylindrical metal element that extends downward from the outer housing 18 and encircles the stem 28 and the reference electrode 30.

FIG. 10 shows the reinforced concrete assessment system 60 in an end view. As is apparent from FIG. 10, the measurement unit 16 can be relatively wide, for example, about the width of a typical road lane, and can comprise multiple Kelvin probes 24 that are aligned in an array along the width of the unit. In such a case, multiple measurements across the width of the concrete surface 20 can be simultaneously recorded. Each Kelvin probe 24 can have the same configuration as that described above in relation to FIG. 9 and each can have its own reference electrode shield 74.

The reinforced concrete assessment system 60 of FIGS. 9 and 10 are particularly useful in bridge deck survey applications. In such a scenario, the system 60 would record the potential reading from each probe 24 across a lane of the bridge along the entire bridge length. Following the usual practice in conventional potential surveys, the results can then be instantly summarized in a color-coded map identifying any highly negative potential spots indicative of active corrosion.

It is noted that, while the system 60 is shown as comprising its own wheels 64 and therefore forming its own trailer, the system could alternatively be integrated into an existing trailer or instrumented diagnostic vehicle.

Figure 11:
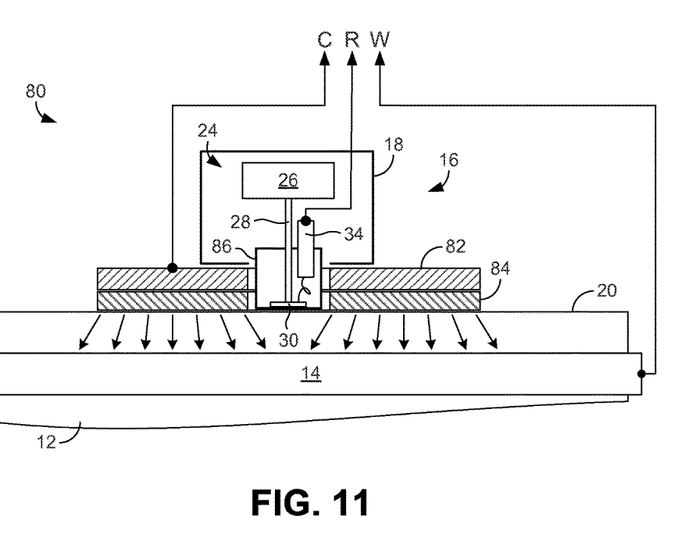
FIG. 11 is a schematic view of a third embodiment of a non-contact reinforced concrete assessment system that includes a Kelvin probe.

Kelvin probes can also be incorporated within non-contact reinforced concrete assessment systems that are configured to determine the rate of corrosion of the steel reinforcement within concrete by means of steel polarization measurements. FIG. 11 illustrates an example of a system 80 suited for that purpose. Similar to the system 10 of FIG. 3, the system 80 shown in FIG. 11 comprises a measurement unit 16 that includes an outer housing 18 that contains or supports a Kelvin probe 24 that comprises a vibration generator 26, a stem 28, a reference electrode 30, and a preamplifier 34. In addition to the measurement unit 16, the system 60 includes a control unit (not shown) that, for example, can include a processing device, memory, a power source, and a display.

Instead of being supported by discrete feet, however, the system 80 of FIG. 11 is supported by a pressure plate 82 that rests on top of an electrically-conductive elastomeric member 84. The pressure plate 82 and the elastomeric member 84 together act as a counter electrode while the steel member 14 acts as the working electrode. In some embodiments, both the pressure plate 82 and the elastomeric member 84 can be circular and have central (e.g., concentric) openings that enable the stem 28 and reference electrode 30 to pass. By way of example, the pressure plate 82 can be made of a metal material such as steel and the elastomeric member 84 can be made of rubber that comprises embedded graphite particles.

With further reference to FIG. 11, the system 80 also includes a grounded metal shield 86 that renders the reference electrode 30 insensitive to potential changes in the pressure plate 82 and the elastomeric member 84. In some embodiments, the shield 86 is cylindrical and encircles the stem 28 and the reference electrode 30.

Although the reinforced concrete assessment systems disclosed herein have been described as being used to assess reinforced concrete roads and bridges, it is noted that the systems can be used in other applications. For example, the systems could be used to assess reinforcement provided within concrete monuments or statues. Indeed, the systems can be adapted to assess reinforcement provided within substantially any concrete structure.

The invention claimed is:

1. A method for non-contact assessment of reinforced concrete that comprises a steel reinforcement member that is embedded in concrete, the method comprising:
   positioning a reference electrode in close proximity to an outer surface of the concrete without contacting the reference electrode to the concrete and without any component extending from the reference electrode to the concrete such that the reference electrode is neither directly nor indirectly in contact with the concrete;
   vibrating the reference electrode with a vibration generator; and
   measuring an electrical potential difference between the reference electrode and the outer surface of the concrete, the potential difference being indicative of the condition of a portion of the steel reinforcement member embedded in the concrete below the outer surface of the concrete at the location of the reference electrode.

2. The method of claim 1, wherein positioning the reference electrode comprises suspending the reference electrode over a horizontal road or bridge surface.

3. The method of claim 1, wherein suspending the reference electrode comprises suspending the reference electrode with a stem that extends downward from the vibration generator.

4. The method of claim 1, wherein vibrating the reference electrode comprises vibrating the reference electrode with an electromagnetic voice coil that linearly displaces the reference electrode in response to a magnetic field generated from current passing through the coil.

5. The method of claim 1, wherein measuring the electrical potential difference comprises applying a voltage to the steel reinforcement member and obtaining a signal from the reference electrode in an absolute measurement scheme.

6. The method of claim 1, wherein measuring the electrical potential difference comprises applying a voltage to the surface of the concrete at a location near the location of the reference electrode and obtaining a signal from the reference electrode in a differential measurement scheme.

7. The method of claim 1, wherein measuring the electrical potential difference comprises applying a voltage to the surface of the concrete at a location near the reference electrode with a counter electrode and obtaining a signal from the reference electrode in a dynamic measurement scheme.

8. The method of claim 1, wherein measuring the electrical potential difference comprises amplifying a signal obtained from the reference electrode.

9. The method of claim 1, wherein measuring the electrical potential difference comprises obtaining a signal from the reference electrode and converting it into an electrical potential.

10. The method of claim 1, wherein positioning the reference electrode in close proximity to the outer surface of the concrete comprises positioning the reference electrode within approximately 0.9 to 1.1 mm of the outer surface of the concrete.

11. The method of claim 1, wherein vibrating the reference electrode comprises linearly displacing the reference electrode toward and away from the outer surface of the concrete.

12. The method of claim 11, wherein vibrating the reference electrode comprises displacing the reference electrode within a range of approximately 0.8 to 1.2 mm between its uppermost and lowermost position.

13. The method of claim 11, wherein vibrating the reference electrode comprises displacing the reference electrode at a frequency of approximately 147 Hz.

14. The method of claim 5, further comprising amplifying the signal using a preamplifier.

\* \* \* \* \*